US00PP23978P2

(12) United States Plant Patent
van Tol

(10) Patent No.: US PP23,978 P2
(45) Date of Patent: Oct. 8, 2013

(54) ***DELPHINIUM* PLANT NAMED 'TESSA'**

(50) Latin Name: *Delphinium elatum*
Varietal Denomination: Tessa

(76) Inventor: Benjamin R. van Tol, Abbenes (NL)

( * ) Notice: Subject to any disclaimer, the term of this patent is extended or adjusted under 35 U.S.C. 154(b) by 92 days.

(21) Appl. No.: 13/385,522

(22) Filed: Feb. 23, 2012

(51) Int. Cl.
*A01H 5/00* (2006.01)

(52) U.S. Cl.
USPC ..... Plt./423

(58) Field of Classification Search
USPC ..... Plt./423
See application file for complete search history.

*Primary Examiner* — Susan McCormick Ewoldt
(74) *Attorney, Agent, or Firm* — Audrey Charles

(57) ABSTRACT

A new and distinct cultivar of *Delphinium* plant named 'Tessa', particularly distinguished by semi-double, deep blue-colored flowers, short, sturdy stems, narrow upright, vigorous growth habit, and very good mildew resistance with good garden performance, is disclosed.

1 Drawing Sheet

Latin name of genus and species of plant claimed: *Delphinium elatum.*

Variety denomination: 'Tessa'.

BACKGROUND OF THE INVENTION

The present invention relates to a new and distinct cultivar of *Delphinium* plant botanically known as *Delphinium elatum* and hereinafter referred to by the cultivar name 'Tessa'. The new *Delphinium* cultivar is a naturally-occurring whole plant mutation. The new cultivar was discovered and selected as a single plant within a population of *Delphinium elatum* plants during 2005 in an outdoor nursery location in Abbenes, The Netherlands.

Asexual reproduction of the new *Delphinium* by vegetative cuttings and divisions in a controlled environment in Abbenes, The Netherlands since 2006, has shown that the unique features of the *Delphinium* are stable and have reproduced true-to-type in successive generations.

SUMMARY OF THE INVENTION

The following are the most outstanding and distinguishing characteristics of this new cultivar when grown under normal horticultural practices in Abbenes, The Netherlands:

1. Semi-double, deep blue-colored flowers;
2. Short, sturdy stems;
3. Narrow upright, vigorous growth habit; and
4. Very good mildew resistance with good garden performance.

Of the many commercially available *Delphinium* cultivars, the most similar in comparison to the new cultivar is 'Darwin's Blue Indulgence', U.S. Plant Pat. No. 13,011. However, in comparison, plants of the new cultivar 'Tessa' differ from plants of 'Darwin's Blue Indulgence' in at least the following characteristics:

1. Plants of the new cultivar have a flower color that is darker than plants of 'Darwin's Blue Indulgence';
2. Plants of the new cultivar have a semi-double flower form that is different from the full-double flower form of plants of 'Darwin's Blue Indulgence'; and 3. Plants of the new cultivar are more resistant to mildew than plants of 'Darwin's Blue Indulgence'.

In addition the new cultivar can be compared to the commercially available cultivar, 'Darwin's Pink Indulgence', U.S. Plant Pat. No. 13,065. However, in comparison, plants of the new cultivar 'Tessa' differ from plants of 'Darwin's Pink Indulgence' in at least the following characteristics:

4. Plants of the new cultivar have a flower color that is different from plants of 'Darwin's Pink Indulgence';
5. Plants of the new cultivar have a semi-double flower form that is different from the full-double flower form of plants of 'Darwin's Pink Indulgence'; and
6. Plants of the new cultivar are more resistant to mildew than plants of 'Darwin's Pink Indulgence'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Tessa'. The plant was field grown for approximately 1 year in Abbenes, The Netherlands in an outdoor nursery location. The plant was transplanted into a container for photography purposes.

DETAILED BOTANICAL DESCRIPTION

Figure 1:
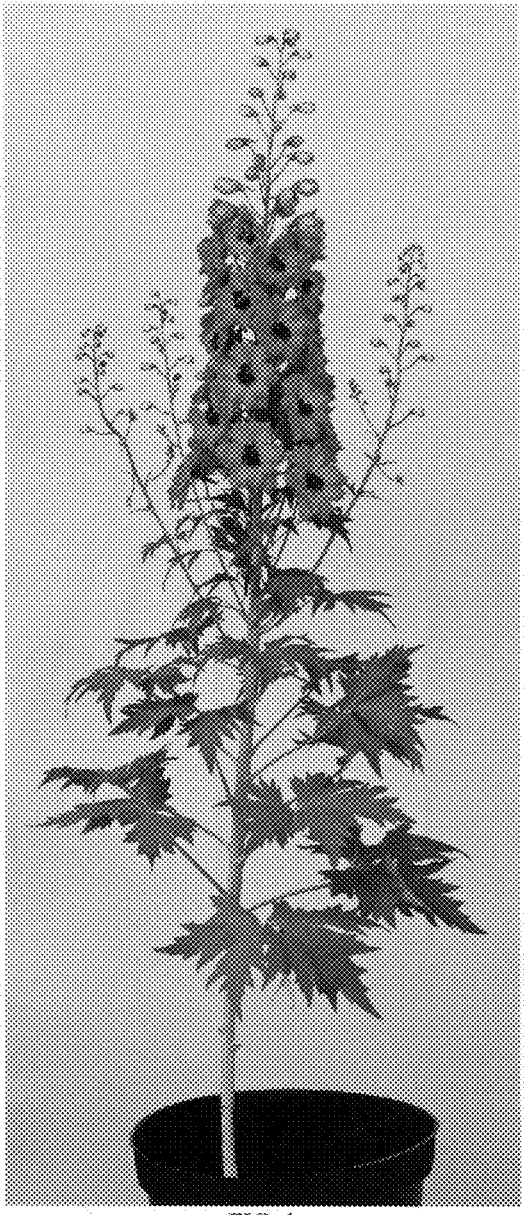
FIG. 1 illustrates a side view of the overall growth and flowering habit of 'Tessa'.
Figure 2:
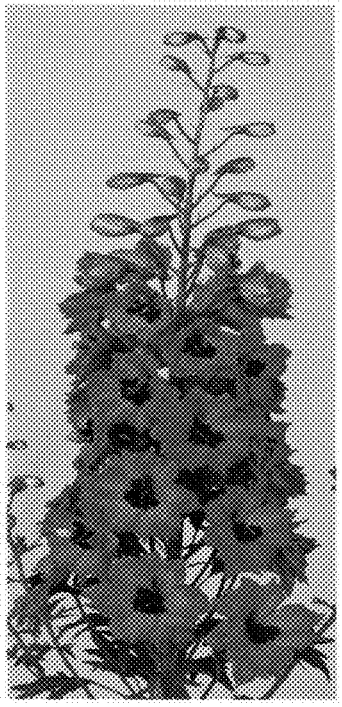
FIG. 2 illustrates a close-up view of an individual inflorescence of 'Tessa'.
Figure 3:
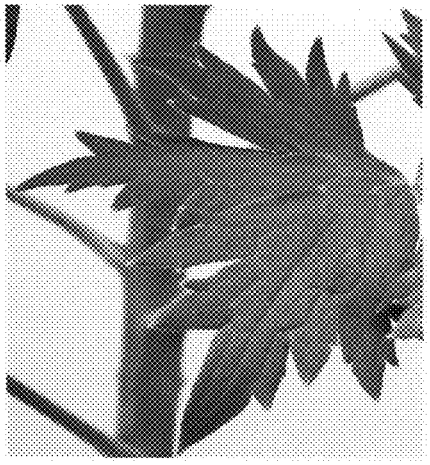
FIG. 3 illustrates a close-up view of the foliage of 'Tessa'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Abbenes, The Netherlands. The plant history was taken in June 2011 on 1-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Delphinium elatum* cultivar 'Tessa'.

Parentage:

*Female parent.*—Unknown *Delphinium elatum.*

*Male parent.*—Unknown *Delphinium elatum.*

Propagation:

*Type cutting.*—Vegetative cutting.

*Time to initiate roots.*—Approximately 14 days with average soil temperature of 20° C.

*Time to produce a rooted cutting.*—Approximately 40 days with average soil temperature of 20° C.

*Root description.*—Grey, thin, fibrous, moderately dense.

*Rooting habit.*—Freely branching.

Plant description:

*Type.*—Herbaceous perennial. Overall shape: Narrow triangle. High temperature tolerance: Tolerant to at least 35° C. Low temperature tolerance: Hardy to at least USDA Zone 4. Excellent garden performance.

*Commercial crop time.*—After rooting, approximately 30 weeks are required to produce a finished flowering plant in a 2-liter container.

*Growth habit and general appearance.*—Narrow upright, vigorous.

*Size.*—Height from soil level to top of plant plane: Approximately 105.0 cm. Width: Approximately 39.3 cm. Rate of growth: In spring, approximately 20 cm per month.

*Branching habit.*—Non-branched; flowering stems grow from base.

*Stem.*—Shape: Rounded, slightly angled. Strength: Very strong. Aspect: Erect. Length to base of inflorescence: Approximately 48.0 cm. Diameter: Approximately 1.3 cm. Length of central internode: Approximately 2.2 cm. Texture: Glabrous with a densely pubescent base, dull. Color of pubescence: 157D. Color of young and mature stems: 146D with stripes of 146A, glaucous layer of 145C.

Foliage description:

*General description.*—Quantity of leaves per stem: Approximately 22. Form: Simple. Arrangement: Alternate. Durability to stress: Moderately high.

*Leaves.*—Shape: Palmately lobed. Margin: Incised. Apex: Acute. Base: Hastate, not overlapping. Venation pattern: Palmate. Length of mature leaf: Approximately 15.5 cm. Width of mature leaf: Approximately 17.7 cm. Texture of upper surface: Smooth, glabrous. Texture of lower surface: Moderately pubescent on margins and venation. Color of pubescence: 157D. Color of upper surface of young foliage: 137A with venation of 144B. Color of lower surface of young and mature foliage: 138B with venation of 144C. Color of upper surface of mature foliage: 137A to 137B with venation of 144B.

*Petiole.*—Shape: Flattened. Length: Approximately 10.1 cm. Width: Approximately 4.0 mm. Height: Approximately 3.0 mm. Color: 144A.

Flowering description:

*Flowering habit.*—Freely flowering under outdoor growing conditions from early to mid-summer.

*Lastingness of flower on the plant.*—Approximately 10 to 14 days.

Inflorescence description:

*General description.*—Type: Terminal raceme. Fragrance: None detected. Height: Approximately 59.0 cm. Width: Approximately 27.8 cm. Quantity of flowers and buds per inflorescence: Approximately 45 for central inflorescence and 17 for secondary inflorescences. Quantity of fully-open flowers per inflorescence: Approximately 28 for central inflorescence and 0 for secondary inflorescences.

*Peduncle.*—Strength: Very strong. Aspect: Erect primary peduncles with secondary peduncles at approximately a 40° angle. Length of primary: Approximately 56.8 cm. Diameter of primary: Approximately 6.0 mm. Texture: Glabrous, smooth. Color: 146D with stripes of 146A, glaucous layer of 145C.

Flower description:

*General description.*—Type: Semi-double, self-cleaning. Shape: Round, somewhat flattened. Aspect: Outward.

*Bud just before opening.*—Shape: Obovate, upper half tapers to a spur. Length excluding spur: Approximately 1.4 cm. Length of spur: Approximately 9.0 mm. Diameter: Approximately 9.0 mm. Color: 122C with 188B and an underside of 145C to 145D. Rate of opening: Approximately 10 days.

*Corolla.*—Arrangement: Whorls of outer and inner sepals and a central whorl of petaloids. Depth (including spur): Approximately 4.6 cm. Diameter: Approximately 7.3 cm.

*Inner sepals.*—Quantity: Approximately 8. Arrangement: Rotate. Appearance: Velvety. Shape: Elliptic to obovate. Margin: Entire to deeply incised. Apex: Broadly acute. Length: Approximately 3.6 cm. Width: Approximately 2.0 cm. Texture of upper and lower surfaces: Smooth, glabrous. Color of upper surface when first open: 96D tinged with N88D, and base of 138D. Color lower surface when first open: 96C and base of 138D. Color of upper surface when fully open: 100A with centers of 91A and base of 138C. Color lower surface when fully open: 96C and 69D, base of 138D.

*Petaloids.*—Arrangement: Central whorl. Quantity: Approximately 7. Shape: Spatulate, one is spurred. Length: Approximately 1.7 cm. Width: Approximately 6.0 mm. Texture: Center pubescence of short hairs having a length of approximately 0.3 mm and color of 156D. Color: 203A with base of 201B to 201D. Length of spur: Approximately 9.0 mm. Width of spur: Approximately 2.0 mm. Color of spur: 147A.

*Calyx* (*outer sepals*).—Shape: Rotate. Depth (including spur): Approximately 4.0 cm. Diameter: Approximately 7.1 cm. Quantity: 5. Appearance: Velvety. Shape: Ovate, with upper sepal spurred. Margin: Entire. Apex: Broadly acute. Length: Approximately 4.0 cm. Width: Approximately 2.5 cm. Length of spur: Approximately 2.3 cm. Width of spur: Approximately 6.0 mm. Texture of upper and lower surfaces:

Smooth, glabrous. Color of upper surface when first open: 100A, margins tinged with 92D, and base of 138D. Color lower surface when first open: 96C with a small circle of 138B near the apex, base of 138D, and spur of 94A to 94B. Color of upper surface when fully open: 100A, margins tinged with 92C to 92D, apex tinged with 92A, and base of 138C. Color lower surface when fully open: 96C and 69D with a small circle of 138B near the apex, base of 138D, and spur of 94A to 94B.

*Pedicel.*—Strength: Strong. Aspect: Approximately at a 35° angle. Length: Approximately 7.9 cm. Diameter: Approximately 2.0 mm. Texture: Smooth, glabrous. Color: 143A.

*Reproductive organs.*—Androecium: Stamen quantity: 40 per flower, basifixed. Anther shape: Kidney-shaped. Anther length: Approximately 1.5 mm. Filament length: Approximately 8.0 mm. Anther color: 203A. Filament color: NN155D. Pollen amount: Moderate. Pollen color: 156D. Gynoecium: Pistil quantity: 4 per flower. Pistil length: Approximately 3.0 mm. Stigma shape: Pointed. Stigma color: NN155D. Style length: Approximately 2.5 mm. Style color: NN155D. Ovary color: N189B.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Delphinium* plant named 'Tessa', substantially as herein shown and described.

* * * * *